US012496237B2

(12) United States Patent
Surushe

(10) Patent No.: US 12,496,237 B2
(45) **Date of Patent: *Dec. 16, 2025**

(54) ABSORBENT ARTICLE WITH WAIST GUARD

(71) Applicant: The Procter & Gamble Company, Cincinnati, OH (US)

(72) Inventor: Abhishek Prakash Surushe, Kelkheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 476 days.

This patent is subject to a terminal disclaimer.

(21) Appl. No.: 17/982,874

(22) Filed: Nov. 8, 2022

(65) Prior Publication Data

US 2023/0172768 A1 Jun. 8, 2023

(30) Foreign Application Priority Data

Dec. 7, 2021 (EP) .................................... 21212845

(51) Int. Cl.

| | |
|---|---|
| ***A61F 13/496*** | (2006.01) |
| ***A61F 13/49*** | (2006.01) |
| ***A61F 13/494*** | (2006.01) |

(52) U.S. Cl.

CPC .... *A61F 13/4963* (2013.01); *A61F 13/49011* (2013.01); *A61F 13/494* (2013.01); *A61F 2013/4948* (2013.01)

(58) Field of Classification Search

CPC .......... A61F 13/51113; A61F 13/49446; A61F 13/494; A61F 13/49466; A61F 13/495; A61F 13/51; A61F 13/49; A61F 13/49012; A61F 2013/4948

See application file for complete search history.

(56) References Cited

U.S. PATENT DOCUMENTS

| | | | | |
|---|---|---|---|---|
| 10,010,458 | B2 | 7/2018 | Barnes | |
| 10,524,962 | B2 | 1/2020 | Raycheck | |
| 10,537,481 | B2 | 1/2020 | Raycheck et al. | |
| 2002/0040215 | A1 | 4/2002 | Suzuki | |
| 2016/0270985 | A1* | 9/2016 | Raycheck | A61F 13/55115 |
| 2020/0038256 | A1* | 2/2020 | Jang | A61F 13/49466 |
| 2021/0154057 | A1 | 5/2021 | Chatterjee et al. | |
| 2021/0267815 | A1* | 9/2021 | Gao | A61F 13/496 |
| 2022/0339044 | A1* | 10/2022 | Surushe | A61F 13/49011 |
| 2023/0172764 | A1* | 6/2023 | Surushe | A61F 13/4758 604/385.3 |
| 2023/0172767 | A1* | 6/2023 | Surushe | A61F 13/495 604/385.3 |

OTHER PUBLICATIONS

PCT Search Report and Written Opinion for PCT/US2022/080880 dated Mar. 15, 2023; 11 pages.

(Continued)

*Primary Examiner* — Michele Kidwell
(74) *Attorney, Agent, or Firm* — Charles R. Matson

(57) ABSTRACT

The invention relates to an absorbent article with a waist guard disposed in the back waist region. The waist guard comprises one or more waist guard sheets, and at least a first and a second pocket. The first pocket is formed by the one or more waist guard sheets, and the second pocket is at least partially provided between the topsheet and the first pocket.

16 Claims, 10 Drawing Sheets

(56) References Cited

OTHER PUBLICATIONS

All Office Actions; U.S. Appl. No. 17/982,908, filed Nov. 8, 2022.
All Office Actions; U.S. Appl. No. 17/982,844, filed Nov. 8, 2022.
Extended EP Search Report and Written Opinion for 21212845.8 dated Jun. 1, 2022, 06 pages.
Unpublished U.S. Appl. No. 17/982,844, filed Nov. 8, 2022, to Abhishek Prakash Surushe.
Unpublished U.S. Appl. No. 17/982,908, filed Nov. 8, 2022, to Abhishek Prakash Surushe.

* cited by examiner

ABSORBENT ARTICLE WITH WAIST GUARD

CROSS-REFERENCE TO RELATED APPLICATIONS

This application claims priority to European Patent Application No. 21212845.8, filed on Dec. 7, 2021, which is herein incorporated by reference in its entirety.

FIELD OF THE INVENTION

The present invention relates to absorbent articles having a waist guard for preventing leakage of low viscosity bodily exudates, while also maintaining other functions as an absorbent article.

BACKGROUND OF THE INVENTION

Infants and other individuals wear absorbent articles such as diapers to receive and contain urine and other body exudates. Pull-on absorbent articles, or pant-type absorbent articles, such as described in PCT Publication WO 2006/17718A, are those which are donned by inserting the wearer's legs into the leg openings and sliding the article up into position about the lower torso. Pant-type absorbent articles have become popular also for younger babies requiring a soft fit around the waist opening and leg openings. Moreover, pant-type absorbent articles have become popular for females having heavy flow or overnight usage during menstruation periods. One function desired for a pant-type article is a protective measure for preventing leakage of low viscosity bodily exudates through the waist opening. Those pant-type articles having less material around the waist opening for breathability purpose or otherwise, may have risk of leakage from the waist opening, particularly when the wearer is lying on his/her back or belly.

Pant-type articles may take various structures wherein the circumference of the waist opening and vicinity thereof is made elastic enough to facilitate the wearer or the caregiver to expand the article and insert the wearer's legs into the leg openings for wearing the article. Accordingly, pant-type articles provide only a very small range of size adjustment or body configuration adjustment based on the structural limitations of the article. As such, pant-type articles are typically so configured to accommodate size and configuration ranges by providing the elastic belt region very stretchable and comfortable to wear, yet with reliable fit such that sufficient protection against sagging and leakage may be provided. It is desired that such basic functions of the elastic belt region may be maintained even with introduction of the aforementioned protective measure.

Based on the foregoing, there is a need for an absorbent article provided with a protective measure for efficiently preventing leakage of low viscosity bodily exudates from the waist opening. There is also a need for providing such an absorbent article which can be economically made.

SUMMARY OF THE INVENTION

The present invention is directed to an absorbent article having a longitudinal centerline and a longitudinal direction along and in parallel to the longitudinal centerline, and having a transverse centerline and a transverse direction along and in parallel to the transverse centerline. The absorbent article has a front waist region with a front waist edge, a back waist region with a back waist edge and a crotch region extending longitudinally between the front and back waist region.

The absorbent article comprises a liquid pervious topsheet, a liquid impervious backsheet, and an absorbent core sandwiched there between.

A waist guard is disposed in attached to the back waist region. The waist guard comprises one or more than one waist guard sheet(s).

The waist guard comprises at least a first and a second pocket. The first pocket is formed by the one or more waist guard sheet(s), and the second pocket is at least partially provided between the topsheet and the first pocket, such that the second pocket is formed by the one or more waist guard sheet(s) and the topsheet.

The first pocket has a first closed base line at or, preferably, adjacent to the back waist edge and extends along the longitudinal direction from the first closed base line towards a first open edge.

The second pocket has a second closed base line at or, preferably, adjacent to the back waist edge and extends along the longitudinal direction from the second closed base line towards a second open edge.

The complete area of each of the first pocket and of the second pocket superpose the backsheet.

The first pocket comprises at least a first elastic portion provided at or adjacent to the first open edge and the second pocket comprises at least a second elastic portion provided at or adjacent to the second open edge.

The second open edge is provided closer to the transverse centerline than the first open edge.

The second waist pocket may have a larger surface area than the first waist pocket. Larger surface area can generally be seen to correlate to higher volume inside the pocket. The surface area of the first pocket is the area that is confined by the first closed base line, the first open edge and the left and right side edges of the first pocket (see description below for details). Similarly, the surface area of the second pocket is the area that is confined by the first closed base line, the first open edge and the left and right side edges of the second pocket.

The surface area of the second pocket may be at least 10%, or at least 20%, or at least 30%, or at least 50%, larger than the surface area of the first pocket. The surface area of the second pocket may not be more than 120%, or more than 100%, or not more than 80% larger than the surface area of the first pocket.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

Figure 1:
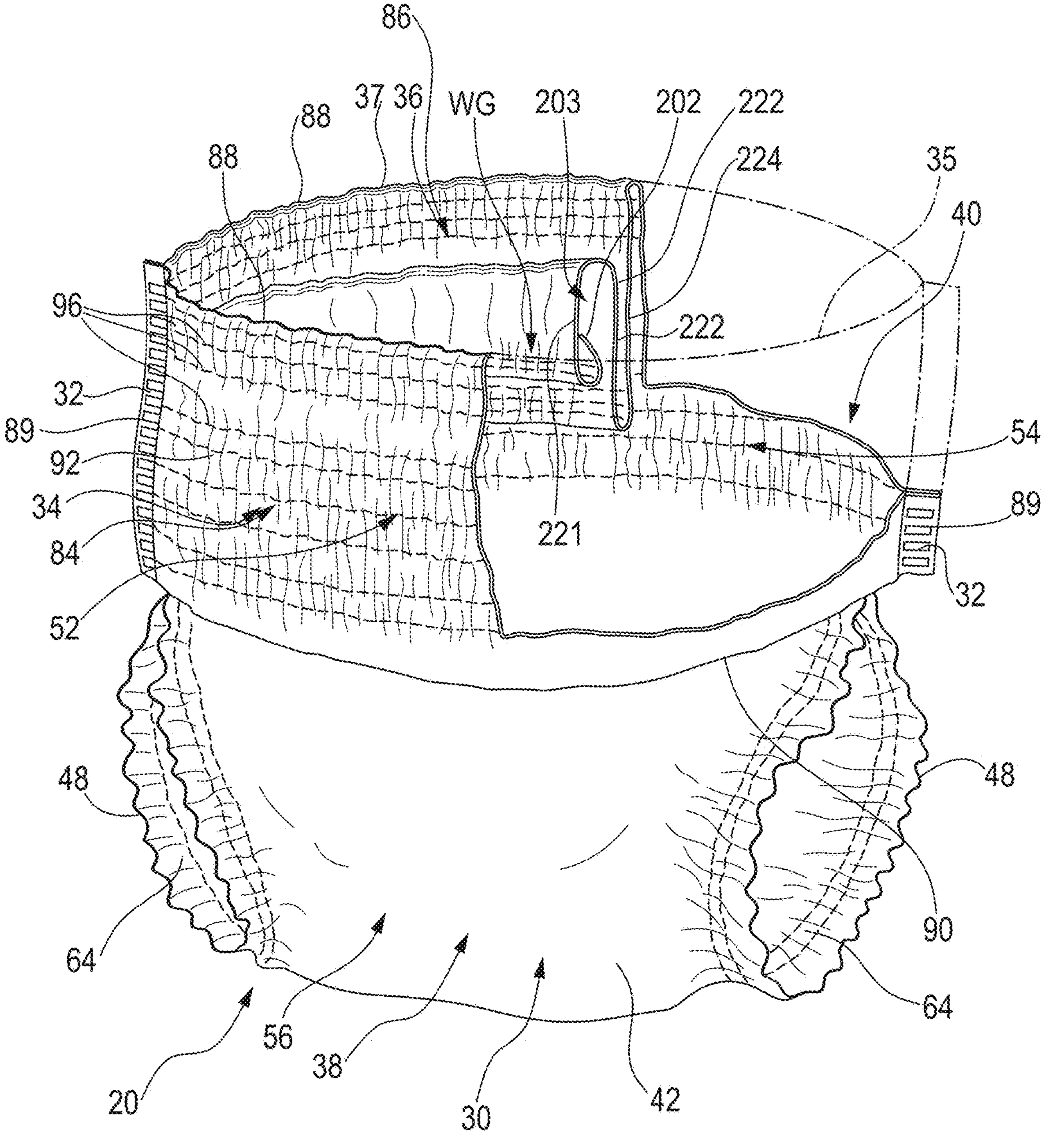
FIG. 1 is a perspective view of one embodiment of an absorbent article of the present invention.

Unless specified differently below, adhesives are designated by reference number 241 in the Figures (adhesive not shown in FIG. 1).

Definitions

As used herein, the following terms shall have the meaning specified thereafter:

"Absorbent article" refers to devices that absorb and contain body exudates, particularly urine and other water-containing liquids, and, more specifically, refers to devices that are placed against or in proximity to the body of the wearer to absorb and contain the various exudates discharged from the body. Absorbent articles may include diapers (for babies and infants as well as for adult incontinence), pants (for babies and infants as well as for adult incontinence). As used herein, the term "exudates" includes, but is not limited to, urine, blood, vaginal discharges, sweat and fecal matter. Preferred absorbent articles of the present invention are disposable absorbent articles, more preferably disposable diapers, disposable pants and disposable absorbent inserts.

"Absorbent core" is used herein to refer to a structure intended to be disposed between a topsheet and backsheet of an absorbent article for absorbing and storing liquid received by the absorbent article.

"Disposable" is used in its ordinary sense to mean an article that is disposed or discarded after a limited number of usage events over varying lengths of time, for example, less than 10 events, less than 5 events, or less than 2 events. If the disposable absorbent article is a diaper, a pant, absorbent insert, sanitary napkin, sanitary pad or wet wipe for personal hygiene use, the disposable absorbent article is most often intended to be disposed after single use. The used and disposed absorbent article may or may not be subsequently recycled.

"Diaper" and "pant" refers to an absorbent article generally worn by babies, infants and incontinent persons about the lower torso so as to encircle the waist and legs of the wearer and that is specifically adapted to receive and contain urinary and fecal waste. In a pant, as used herein, the longitudinal edges of the first and second waist region are attached to each other to a pre-form waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (e.g., seam, weld, adhesive, cohesive bond, fastener, etc.). A pant may be pre-formed anywhere along the circumference of the article (e.g., side fastened, front waist fastened). In a diaper, the waist opening and leg openings are only formed when the diaper is applied onto a wearer by (releasable) attaching the longitudinal edges of the first and second waist region to each other on both sides by a suitable fastening system.

"Longitudinal" refers to a direction running substantially perpendicular from a waist edge to an opposing waist edge of the article and generally parallel to the maximum linear dimension of the article. "Transverse" refers to a direction perpendicular to the longitudinal direction.

"Inner" and "outer" refer respectively to the relative location of an element or a surface of an element or group of elements. "Inner" implies the element or surface is nearer to the body of the wearer during wear than some other element or surface. "Outer" implies the element or surface is more remote from the skin of the wearer during wear than some other element or surface (i.e., element or surface is more proximate to the wearer's garments that may be worn over the present article).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Hydrophilic" describes surfaces of substrates which are wettable by aqueous fluids (e.g., aqueous body fluids) deposited on these substrates. Hydrophilicity and wettability are typically defined in terms of contact angle and the strike-through time of the fluids, for example through a nonwoven fabric. This is discussed in detail in the American Chemical Society publication entitled "Contact Angle, Wettability and Adhesion", edited by Robert F. Gould (Copyright 1964). A surface of a substrate is said to be wetted by a fluid (i.e., hydrophilic) when either the contact angle between the fluid and the surface is less than 90°, or when the fluid tends to spread spontaneously across the surface of the substrate, both conditions are normally co-existing. Conversely, a substrate is considered to be "hydrophobic" if the contact angle is equal to or greater than 90° and the fluid does not spread spontaneously across the surface of the fiber. The contact angle test method used for the present invention is set out herein below.

"Extendibility" and "extensible" mean that the width or length of the component in a relaxed state can be extended or increased.

"Elasticated" and "elasticized" mean that a component comprises at least a portion made of elastic material.

"Elongation rate" means the state of elongation of a material from its relaxed, original length, namely an elongation rate of 10% means an elongation resulting in 110% of its relaxed, original length.

"Elongatable material", "extensible material", or "stretchable material" are used interchangeably and refer to a material that, upon application of a biasing force, can stretch to an elongation rate of at least 10% (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastic." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "non-elastic". For example, an elongatable material that has an initial length of 100 mm can extend at least to 150 mm, and upon removal of the force retracts to a length of at least 145 mm (i.e., exhibiting a 10% recovery).

As used herein, the term "nonwoven web" refers to a material which is a manufactured web/layer of directionally or randomly oriented fibers or filaments. The fibers may be of natural or man-made origin. Natural fibers may be selected from the group consisting of wood pulp fibers, wheat straw fibers, rice straw fibers, flax fibers, bamboo fibers, cotton fibers, jute fibers, hemp fibers, sisal fibers, bagasse fibers, Hesper aloe fibers, miscanthus, marine or fresh water algae/seaweeds, silk fibers, wool fibers, and combinations thereof. Another group of fibers may also be regenerated cellulose fibers, such as viscose, Lyocell (Tencel®), rayon, modal, cellulose acetate fibers, acrylic fibers, cuprammonium rayon, regenerated protein fibers etc. Preferably, the natural fibers or modified natural fibers are selected from the group consisting of cotton fibers, bamboo fibers, viscose fibers or mixtures thereof. Preferably, the natural fibers are cotton fibers. Synthetic fibers may be selected from the group consisting of polyolefins (such as polyethylene, polypropylene or combinations and mixtures thereof), polyethylene terephthalate (PET), co PET, polylactic acid (PLA), polybutylene succinate (PBS), polyhydroxy alkanoates (PHA), nylon (or polyammide), or mixtures or combinations thereof. An alternative option is to use superabsorbent fibers, for example SAF™ which is a cross-linked terpolymer based on acrylic acid, which is partially neutralised to its sodium salt, commercially available from Technical Absorbents.

The fibers in a nonwoven web are consolidated by friction, and/or cohesion and/or adhesion, and/or by heat bonding, pressure bonding, heat and pressure bonding, and/or ultrasonic bond excluding paper and products which are woven, knitted, tufted, stitch-bonded. The fibers may be staple fibers (e.g. in carded nonwoven webs) or continuous fibers (e.g. in spunbonded or meltblown nonwoven webs).

Nonwoven webs can be formed by many processes such as meltblowing, spunlaying, solvent spinning, electrospinning, and carding, and the fibers can be consolidated, e.g. by hydroentanglement (in spunlaced nonwoven webs), air-through bonding (using hot air that is blown through the fiber layer in the thickness direction), needle-punching, one or more patterns of bonds and bond impressions created through localized compression and/or application of heat or ultrasonic energy, or a combination thereof. The fibers may, alternatively or in addition, be consolidated by use of a binder. The binder may be provided in the form of binder fibers (which are subsequently molten) or may be provided in liquid, such as a styrene butadiene binder. A liquid binder is provided to the fibers (e.g. by spraying, printing or foam application) and is subsequently cured to solidify.

The basis weight of nonwoven webs is usually expressed in grams per square meter ($g/m^2$).

In a spunlace nonwoven web the fibers have been carded as precursor web and then subjected to hydroentanglement to intermingle and intertwine the fibers with each other. Cohesion and the interlacing of the fibers with one another may be obtained by means of a plurality of jets of water under pressure passing through a moving fleece or cloth and, like needles, causing the fibers to intermingle with one another (hereinafter also referred to as "hydraulic interlacing"). Thus, consolidation of a spunlace nonwoven web is essentially a result of hydraulic interlacing. "Spunlace nonwoven web", as used herein, also relates to a nonwoven formed of two or more precursor webs, which are combined with each other by hydraulic interlacing.

The two or more precursor webs, prior to being combined into one nonwoven by hydraulic interlacing, may have underdone bonding processes, such as heat and/or pressure bonding by using e.g. a patterned calendar roll and an anvil roll to impart a bonding pattern. However, the two or more webs are combined with each other solely by hydraulic interlacing. Alternatively, the spunlace nonwoven web is a single web, i.e. it is not formed of two or more precursor webs. Still in another alternative, the spunlace nonwoven web of the present invention may be formed of one precursor web onto which staple fibers are laid down. The staple fibers may not have been consolidated into a self-sustaining precursor web but the fibers are loosely laid onto the precursor web. The relatively loose staple fibers are then integrated and intertwined with each other and with the fibers of the underlying precursor web by (only) hydraulic interlacing. Spunlace nonwoven layers/webs can be made of staple fibers or continuous fibers (continuous fibers are also often referred to as filaments).

Through-air bonding (interchangeably used with the term "air-through bonding") means a process of bonding staple fibers or continuous fibers by forcing air through the nonwoven web, wherein the air is sufficiently hot to melt (or at least partly melt, or melt to a state where the fiber surface becomes sufficiently tacky) the polymer of a fiber or, if the fibers are multicomponent fibers, wherein the air is sufficiently hot to melt (or at least partly melt, or melt to a state where the fiber surface becomes sufficiently tacky) one of the polymers of which the fibers of the nonwoven web are made. The melting and re-solidification of the polymer provide the bonding between different fibers.

"Comprise," "comprising," and "comprises" are open ended terms, each specifies the presence of the feature that follows, e.g. a component, but does not preclude the presence of other features, e.g. elements, steps, components known in the art or disclosed herein. These terms based on the verb "comprise" encompasses the narrower terms "consisting essential of" which excludes any element, step or ingredient not mentioned which materially affect the way the feature performs its function, and the term "consisting of" which excludes any element, step, or ingredient not specified.

"Adjacent" and "adjacent to", as used herein, means very near or in close proximity "adjacent" may mean spaced by a distance of no more than 50 mm, or not more than 40 mm, or not more than 30 mm, or not more than 25 mm, or not more than 20 mm, or not more than 15 mm, or not more than 10 mm, or not more than 5 mm. For example, if the absorbent article is a relatively large absorbent article intended for adult incontinent wearers, "adjacent" may mean spaced by a distance of no more than 50 mm. In another example, where the absorbent article is intended to be worn by babies, "adjacent" may mean spaced by a distance of not more than 25 mm, or not more than 20 mm, or not more than 15 mm, or not more than 10 mm, or not more than 5 mm.

DETAILED DESCRIPTION OF THE INVENTION

FIG. 1 is a perspective view of an absorbent article 20 of the present invention. The absorbent article 20 has a longitudinal centerline which also serves as the longitudinal axis, and a transverse centerline which also serves as the transverse axis. While th longitudinal centerline notionally divides the absorbent article into left and right halfes of equal width, the transverse axis, extending through the crotch region of the absorbent article and being perpendicular to the longitudinal axis, notionally divides the absorbent article into front and back halfs having equal length. The absorbent article 20 has a body facing surface, a garment facing surface, a front waist region 34 with a front waist edge 35 (the front waist region e.g. being a front elastic belt 84), a back waist region 36 with a back waist edge 37 (the back waist region e.g. being a back elastic belt 86), a crotch region 30 extending longitudinally between the front and back waist region 34, 36. The absorbent article may have side seams 32 which may join the front elastic belt 84 and the back elastic belt 86, to form two leg openings and a waist opening.

The absorbent article 20 may be a pant with a ring-like elastic belt 40 (herein referred to as "belt-type pant") comprising an absorbent main body 38 to cover the crotch region 30 of the wearer, a front elastic belt 84 and a back elastic belt 86. The absorbent main body 38 extends into and overlaps with the front and back elastic belt 84, 86. The front and back elastic belts 84, 86 may form a discrete ring-like elastic belt 40 extending transversely defining the waist opening and being discontinuous in the longitudinal direction. For the belt-type pant, the discrete ring-like elastic belt 40 may also be referred to as the elastic belt 40. For the belt-type pant as exemplified in FIG. 1, the front and back elastic belts 84, 86 and the absorbent main body 38 jointly define the leg openings.

For a pant, the front elastic belt 84 is the front waist region 34, and the back elastic belt 86 is the back waist region 36, and the remainder is the crotch region 30.

While not shown, the absorbent article 20 may be a so-called uni-body type pant configured such that the outer cover layer of the absorbent main body 38 and the garment facing layer of the elastic belt 40 are common. For the uni-body type pant, the portion extending in the transverse direction between the side seams 32, respectively, are considered the front waist region 34 and the back waist region 36, and the remainder is the crotch region 30. For the uni-body type pant, the front waist region 34 is considered the front elastic belt 84, and the back waist region 36 is considered the back elastic belt 86.

The absorbent article 20 comprises a topsheet 24, a backsheet 26 and an absorbent core 62 disposed between the topsheet and the backsheet. The topsheet, backsheet and absorbent core may jointly be referred to as "absorbent main body" 38. The absorbent main body 38 may further comprise an outer cover layer 42 for covering the garment-facing side of the backsheet 26. The topsheet 24 may be a water permeable substrate. The backsheet 26 may be a water impermeable film. The outer cover layer 42 may be a nonwoven web. The absorbent main body 38 comprises an absorbent core 62 for absorbing and containing body exudates disposed on the absorbent main body 38. The topsheet 24 and backsheet 26 may be have a larger longitudinal and transverse dimension than the absorbent core 62, and the absorbent core may be surrounded by the topsheet, and the backsheet. The absorbent main body 38 may have a generally rectangular shape, left and right longitudinally extending side edges 48 and front and back transversely extending end edges 50. The absorbent core 62 may exist through the entire longitudinal dimension of the crotch region 30 and extend partly in the front and back waist regions 34, 36. The absorbent main body 38 may have a front waist panel 52 positioned in the front waist region 34 of the absorbent article 20, a back waist panel 54 positioned in the back waist region 36, and a crotch panel 56 between the front and back waist panels 52, 54 in the crotch region 30. The crotch panel 56 forms the crotch region 30. The center of the front elastic belt 84 may be joined to a front waist panel 52 of the absorbent main body 38, the center of the back elastic belt 86 may be joined to a back waist panel 54 of the absorbent main body 38. The front and back elastic belts 84, 86 may each have a left side panel and a right side panel 82 where the absorbent main body 38 does not overlap. In a pant, the front elastic belt 84 is indirectly joined to the back elastic belt 86 along the longitudinal dimension by the absorbent main body 38.

The absorbent core 62 is intended to store the liquid that enters the absorbent article during use (thus generally having the most absorbent capacity) and that comprises an absorbent material. In some instances, absorbent material may be positioned within a so-called core bag or a core wrap, such as a nonwoven web (the core bag or core wrap being comprised by the absorbent core). The absorbent material may be profiled or not profiled, especially along the longitudinal centerline, depending on the specific absorbent article. "Profiled" means that the absorbent material is not homogene-ously distributed across the surface area of the absorbent core. The absorbent core may comprise, consist essentially of, or consist of, a core wrap, and absorbent material enclosed within the core wrap. The absorbent material may, for example, comprise or consist of a) superabsorbent polymer material, such as superabsorbent polymer particles, or b) a mixture of superabsorbent polymer particles and cellulose fibers, or c) only cellulose fibers, or d) a high internal phase emulsion foam, or e) combinations of any of a) to d). In some instances, the absorbent material may comprise at least 80%, at least 85%, at least 90%, at least 95%, at least 99%, or up to 100% superabsorbent polymers, by weight of the absorbent material. In such instances, the absorbent material may be free of cellulose fibers, or at least mostly free of cellulose fibers. The superabsorbent polymer material may be immobilized by adhesive, such as by adhesive fibers. The absorbent core periphery, which may be the periphery of the core wrap, may define any suitable shape, such as rectangular "T," "Y," "hour-glass," or "dog-bone" shaped, for example. Preferably, the absorbent core has a rectangular shape. An absorbent core periphery having a generally "dog bone" or "hour-glass" shape may taper along its width towards the crotch region of the absorbent article.

The absorbent core may have areas with reduced caliper (wherein the term "reduced" includes areas with no caliper, i.e. areas free of the material of the absorbent core). Areas with reduced caliper may be areas having little or no absorbent material, where a body-facing surface of the core bag may be joined to a garment-facing surface of the core bag. These areas having little or no absorbent material may be referred to as "channels". These channels can embody any suitable shapes and any suitable number of channels may be provided. In other instances, though less preferred, the absorbent core may be embossed to create the impression of channels.

At least one acquisition and distribution layer (ADL) may be provided between the topsheet and the absorbent core. The ADL comprises acquisition materials which are typically hydrophilic materials that provide significant wicking of bodily exudates. These materials may dewater the topsheet and quickly move bodily exudates into the absorbent core. The acquisition materials of the ADL may comprise one or more nonwoven materials, foams, cellulosic materials, cross-linked cellulosic materials, air laid cel-lulosic nonwoven materials, spunlace materials, or combinations thereof, for example. Typically, the one or more layers of the ADL may each have a width and length that are smaller than the width and length of the topsheet. The ADL may have one or more areas with reduced caliper ((wherein the term “reduced” includes areas with no caliper, i.e. areas free of the material of one, more than one, or all layers of the ADL), such as channels, as described above with reference to the absorbent core (including the embossed version). The channels in the ADL may align or not align with channels in the absorbent core. In an example, a first layer of the ADL may comprise a nonwoven material and as second layer of the ADL may comprise a cross-linked cellulosic material. The second layer of the ADL may be provided between the first layer of the ADL and the absorbent core. The first layer of the ADL may be provided between the topsheet and the second layer of the ADL.

Referring to FIG. 1, the absorbent main body 38 may comprise leg cuffs 64 made of material having high fluid impermeability, and elasticized to provide a barrier along both transverse edges of the absorbent main body 38. Such leg cuffs 64 may be attached to the remainder of the absorbent main body by bonding them to the topsheet 24 at both longitudinal edges of the absorbent main body 38, such that at least in the crotch region 30, the leg cuffs are in active elasticity to provide gasketing around the leg openings. The leg cuffs may be folded around the longitudinal edges (i.e. the side edges) of the absorbent main body, such that a portion of the leg cuffs is attached to the garment-facing surface of the backsheet, and/or to the garment-facing surface of the optional outer cover layer.

The elastic belt 40 of the absorbent article of the present invention acts to dynamically create fitment forces and to distribute the forces dynamically generated during wear. The front and back elastic belts 84, 86 may be joined with each other only at the side edges 89 to form side seams 32, a waist opening and two leg openings (such that the waist opening is formed by the front waist edge and the back waist edge of the absorbent article). Each leg opening may be provided with elasticity around the perimeter of the leg opening. The elasticity around the leg opening may be provided by the combination of elasticity from the front elastic belt 84, the back elastic belt 86, and the leg cuffs 64.

The longitudinal length of the backsheet 26 and the outer cover layer 42 may be the same, or may be varied. For example, the outer cover layer 42 may have a shorter length compared to that of the backsheet 26, such that the outer cover layer 42 is devoid where the absorbent main body 38 overlaps the elastic belt 40. By such configuration, the elastic belt may have better breathability. Further, such configuration may provide cost saving. The transverse width of the backsheet 26 and the outer cover layer 42 may be the same, or may be varied. For example, the backsheet 26 may have a shorter transverse width compared to that of the outer cover layer 42. By such configuration, the longitudinal side edges 48 of the crotch panel 56, which make part of the leg openings, may have better breathability. Further, such configuration may provide cost saving.

For the belt-type pant, the longitudinal length LB of the back elastic belt 86 and the longitudinal length LF of the front elastic belt 84 may be provided the same, or the back elastic belt 86 may have a greater longitudinal length LB. When the absorbent article is assembled to form the waist opening and the leg openings, the absorbent article 20 is folded along the transverse centerline such that the front distal edge 88 is aligned with the back distal edge 88 (the front distal edge being the front waist edge 35 and the back distal edge being the back waist edge 37). The front side edge 89 is also aligned with a portion of the back side edge 89. Then the front elastic belt 84 and the back elastic belt 86 are joined at the front and back side edges 89 at the seams 32. The front and back proximal edges 90 of the front and back elastic belt 84, 86, however, may not be aligned to one another. The back proximal edge 90 of the back elastic belt 86 may be disposed longitudinally closer than the front proximal edge 90 of the front elastic belt 84 relative to the transverse centerline such that the proximal portion of the back side panel 82 extends toward the crotch panel 56 of the main body 38 beyond the front proximal edge 90. The side edge of the proximal portion of the back side panel 82 may not be joined to anywhere and free from attachment. Thus, the proximal portion of the back side panel 82 provides a buttock cover 95 (not shown). In such embodiments, the front waist region 34 is smaller than the back waist region 36 along the longitudinal dimension of the absorbent article.

The front elastic belt 84 and back elastic belt 86 are configured to impart elasticity to the belt 40. The front elastic belt 84 and the back elastic belt 86 may each comprise a laminate, the laminate comprising a plurality of elastic members 96, such as elastic strands, running in the transverse direction, an inner sheet 94, an outer sheet 92. The back elastic belt (and also the front elastic belt) may comprise an outer sheet fold 931 which is an extension of the outer sheet 92 and is formed by folding an extension 93 of the outer sheet 92 material at the distal edge 88 of the front and back elastic belts 82, 84; wherein the belt elastic members 96, such as elastic strands, are sandwiched between the inner and outer sheet 94, 92. The front elastic belt 84 and the back elastic belt 86 may each be made only by elastic members 96, such as elastic strands, the inner sheet 94, the outer sheet 92, and the outer sheet fold 931, and, optionally, by adhesive to attach the inner and outer sheet to each other and/or to attach the elastic strands to the inner and/or outer sheet. The belt elastic members 96, such as elastic strands, may extend in the transverse direction to provide a ring like elastic belt 40 when the front elastic belt 84 and the back elastic belt 86 are joined along side seams 32. At least some of the elastic members 96F, 96S 96, such as elastic strands, extend in the transverse direction substantially parallel to each other. All of the elastic members 96F, 96S 96, such as elastic strands, may extend in the transverse direction substantially parallel to each other. Such an article may be economically made. The front and back elastic belt 84, 86 each may have transversely continuous proximal and distal edges, the proximal edge 90 being located closer than the distal edge 88 relative to the longitudinal center of the article. At least 10%, or at least from about 15% to not more than about 70%, of the front and back elastic belts from the waist opening in the longitudinal direction may be a laminate in active elasticity along the entire transverse dimension LW of the front and back elastic belts 84, 86. For each front and back elastic belt 84, 86, the region overlapping the front and/or back waist panel 52, 54 of the absorbent main body 38 may be removed of its elastic activity. Such region removed of elastic activity is referred herein as the "elastic cut window", and the remainder of the intact elastic member capable of imparting elasticity is defined as the "effective length of elasticity of an elastic member".

The tensile stress (N/m) of the entirety of the front and back elastic belts 84, 86, respectively, may be profiled in order to provide the functional benefits of the present invention, such as ease of stretch and application, while also maintaining certain force during wear, to prevent the article from sagging after loading. When the elasticity of the front and back elastic belts 84, 86 are provided by a plurality of elastic members 96, such as elastic strands, running in the transverse direction, the tensile stress may be adjusted by one or more of the following methods; 1) elongation rate of the elastic member 96; 2) density (dtex) of the elastic member 96; 3) longitudinal pitch of multiple elastic members 96; and 4) effective length of elasticity of the elastic member 96 in the transverse direction. By elongation, "0% elongation" is meant the original length of the elastic member.

Alternatively to being a pant, the absorbent article may be a so-called taped diaper, i.e. an absorbent article provided with a fastening system to close the absorbent article around the waist of the wearer. A taped diaper may comprise back ears in the back waist region. The back ears may comprise fasteners and may extend from the back waist region of the absorbent article and attach (using the fasteners) to the landing zone area or landing zone material on a garment-facing portion of the front waist region of the absorbent article. The absorbent article may also have front ears in the front waist region.

The landing zone area may be in the back waist region if the absorbent article fastens from front to back or, preferably, may be in the front waist region if the absorbent article fastens back to front. In some instances, the landing zone may be or may comprise one or more discrete nonwoven materials that are attached to a portion of the garment-facing surface (e.g. on an outer cover nonwoven) of the front waist region or of the back waist region, depending upon whether the absorbent article fastens in the front or the back. In essence, the landing zone is configured to receive the fasteners and may comprise, for example, a plurality of loops configured to be engaged with, a plurality of hooks on the fasteners, or vice versa.

The absorbent article may have front and/or back ears in a taped diaper context. Only one set of ears may be required in most taped diapers. The single set of ears may comprise fasteners configured to engage the landing zone or landing zone area. If two sets of ears are provided, in most instances, only one set of the ears may have fasteners (preferably the back ears), with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material, the backsheet, and/or the topsheet) or may be discrete components attached to absorbent main body on a wearer-facing surface, on the garment-facing surface, or intermediate the two surfaces.

Waist Guard

The absorbent article of the present invention comprises a waist guard WG, which is disposed in and attached to the back waist region 36 such that at least a first pocket 203 and a second pocket 204 are formed. The waist guard WG comprises one or more waist guard sheets 200. The first pocket 203 is formed by the one or more waist guard sheets and the second pocket 204 is at least partially provided between the topsheet and the one or more waist guard sheets.

The first pocket 203 extends along the longitudinal direction from a first closed base line 205 at or adjacent to the back waist edge 37 towards a first open edge. 206. The first closed base line 205 may be longitudinally offset from the back waist edge 37 (towards the transverse centerline) by at least 3 mm, or at least 5 mm. The first closed base line 205 is longitudinally spaced from the first open edge 206, such that the first open edge 206 is closer to the transverse centerline of the absorbent article 20 than the first closed base line 205.

The second pocket 204 extends along the longitudinal direction from a second closed base line 207 at or adjacent to the back waist edge 37 towards a second open edge. 208. The second closed base line 207 may be longitudinally offset from the back waist edge 37 (towards the transverse centerline) by at least 3 mm, or at least 5 mm.

The first closed base line 205 may be longitudinally offset from the second closed base line 207 (towards the transverse centerline) by at least 2 mm, or by at least 3 mm, or by at least 5 mm.

The second closed base line 207 is longitudinally spaced from the second open edge 208, such that the second open edge 208 is closer to the transverse centerline of the absorbent article 20 than the second closed base line 207.

The complete area of the first pocket 203 and of the second pocket 204 superposes the backsheet 26.

The one or more than one waist guard sheet(s) 200 may be a nonwoven web. The waist guard sheet 200 may have at least three fold lines 210, 211, 212, the fold lines may extend substantially parallel to the transverse direction of the absorbent article. The waist guard sheet 200 may have a first end edge 201 and a second end edge 202, both end edges may extend parallel to the transverse centerline of the absorbent article. The waist guard sheet 200 may be a rectangular sheet. The waist guard WG may be formed of a single waist guard sheet 200.

A first and a third fold line 210, 212 may both be provided towards the crotch region 30, a second fold line 211 may be provided towards the back waist edge 37. The first fold line 210 may define the first open edge 206 of the first pocket 203. The second fold line 211 may preferably not be formed at the back waist edge 37 of the absorbent article, but may be, at least slightly (such as by at least 3 mm, or by at least 5 mm), longitudinally offset from the back waist edge 37 towards the transverse centerline.

Due to the first, second and third fold lines 210, 212, the waist guard sheet 200 may comprise at least a first, second, third and fourth portion 220, 221, 222, 223. The first portion 220 may extend from the first fold 210 line towards the back waist edge 37, the second portion 221 may extend between and is confined by the first fold line 210 and the second fold line 211, the third portion 222 may extend between and is confined by the second fold line 211 and the third fold line 212; and the fourth portion 223 may extend from the third fold line 212 towards the back waist edge 37. The fourth portion 223 may be provided between the topsheet 24 and the first portion 220.

The first pocket 203 comprises at least a first elastic portion 230, the first elastic portion 230 being provided along and/or adjacent to the first open edge 206.

Figure 2:
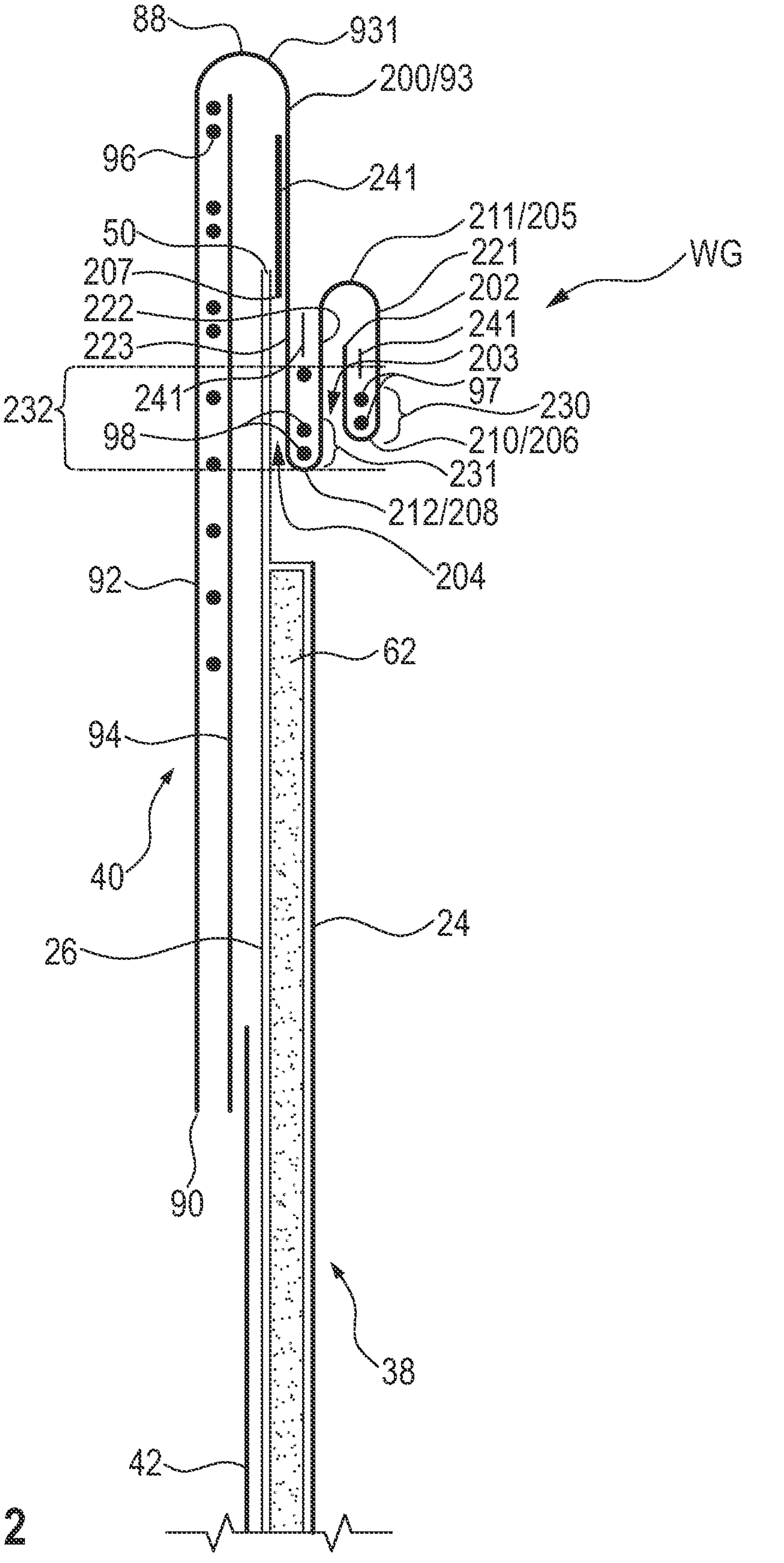
FIG. 2 is a schematic cross section view of the embodiment of FIG. 1.
Figure 3:
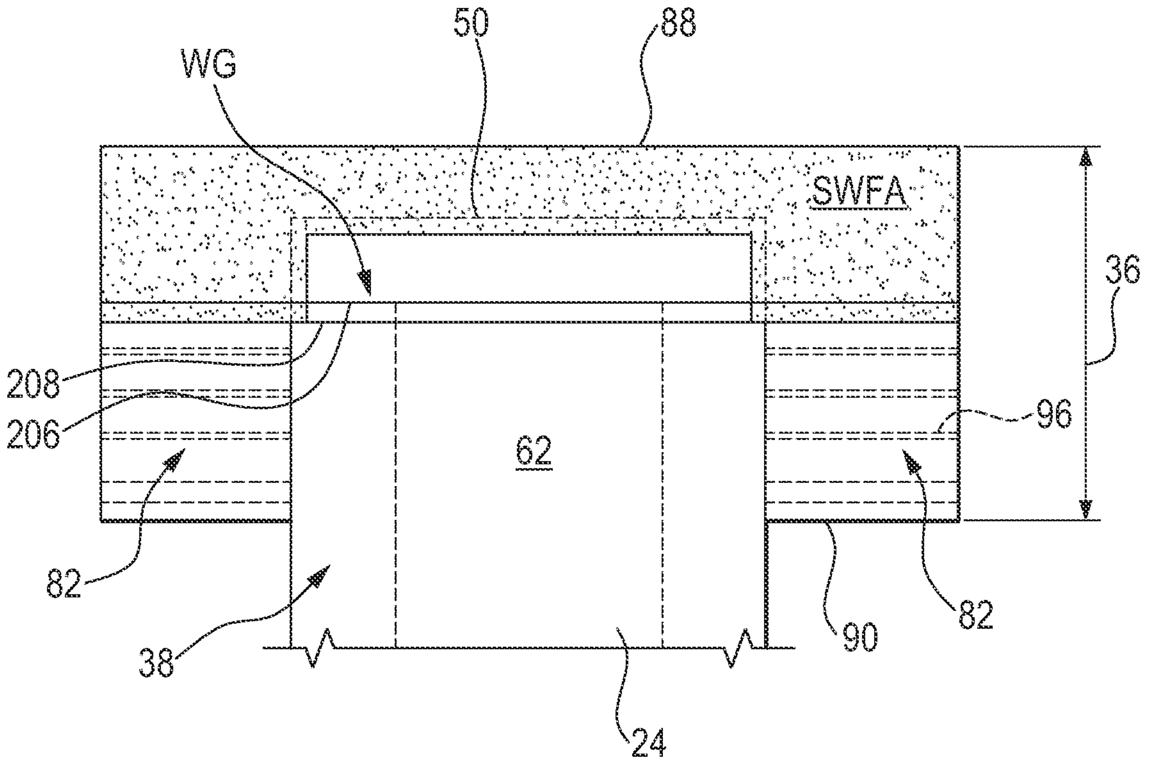
FIG. 3 is an schematic plan views of the back belt and a portion of the absorbent main body of the embodiment of FIG. 1, in a flat uncontracted condition showing the body facing surface.v
Figure 4A:
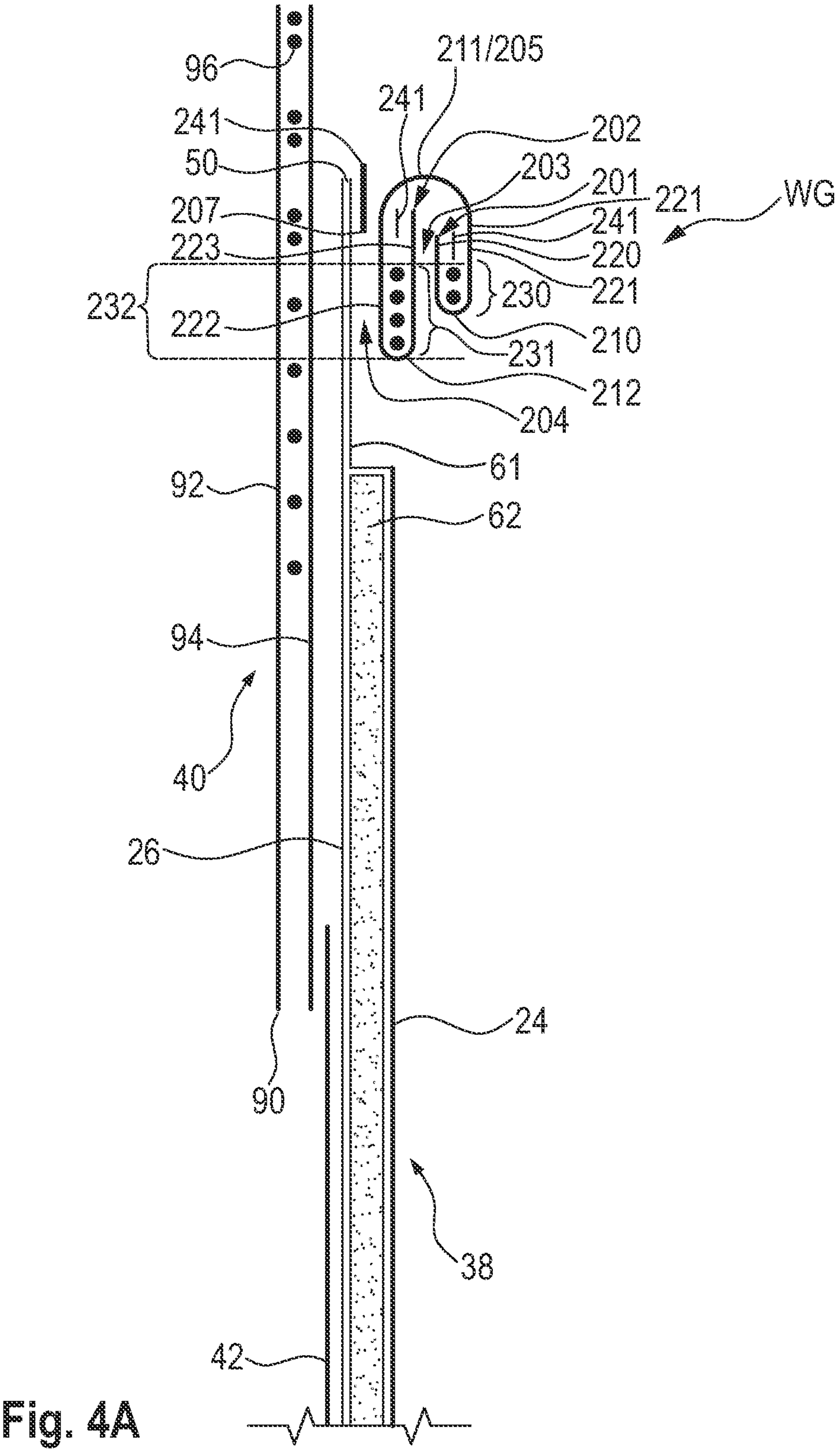
FIGS. 4A-4G are schematic cross section views of of alternative embodiments of absorbent articles of the present invention.
Figure 4B:
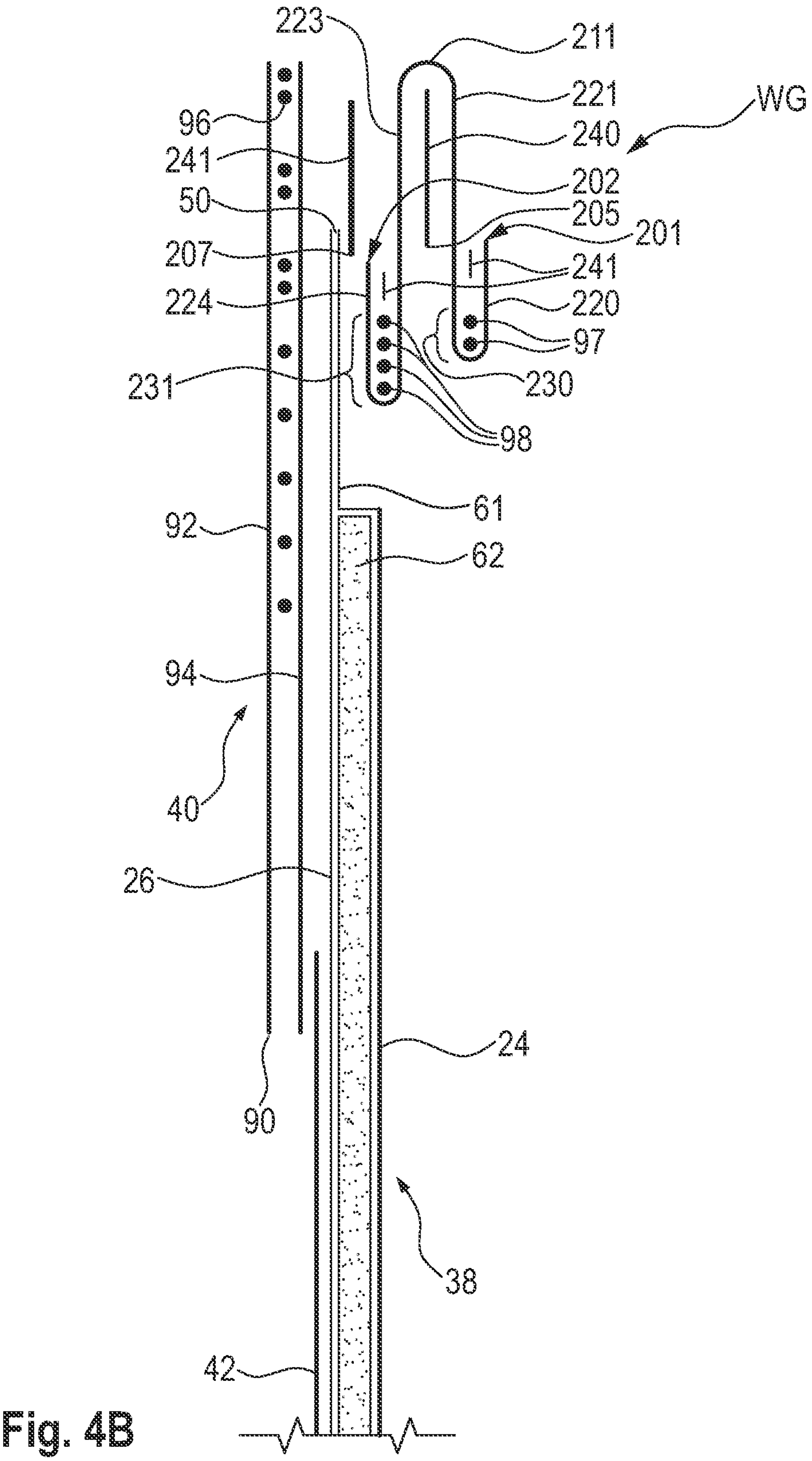
Figure 4C:
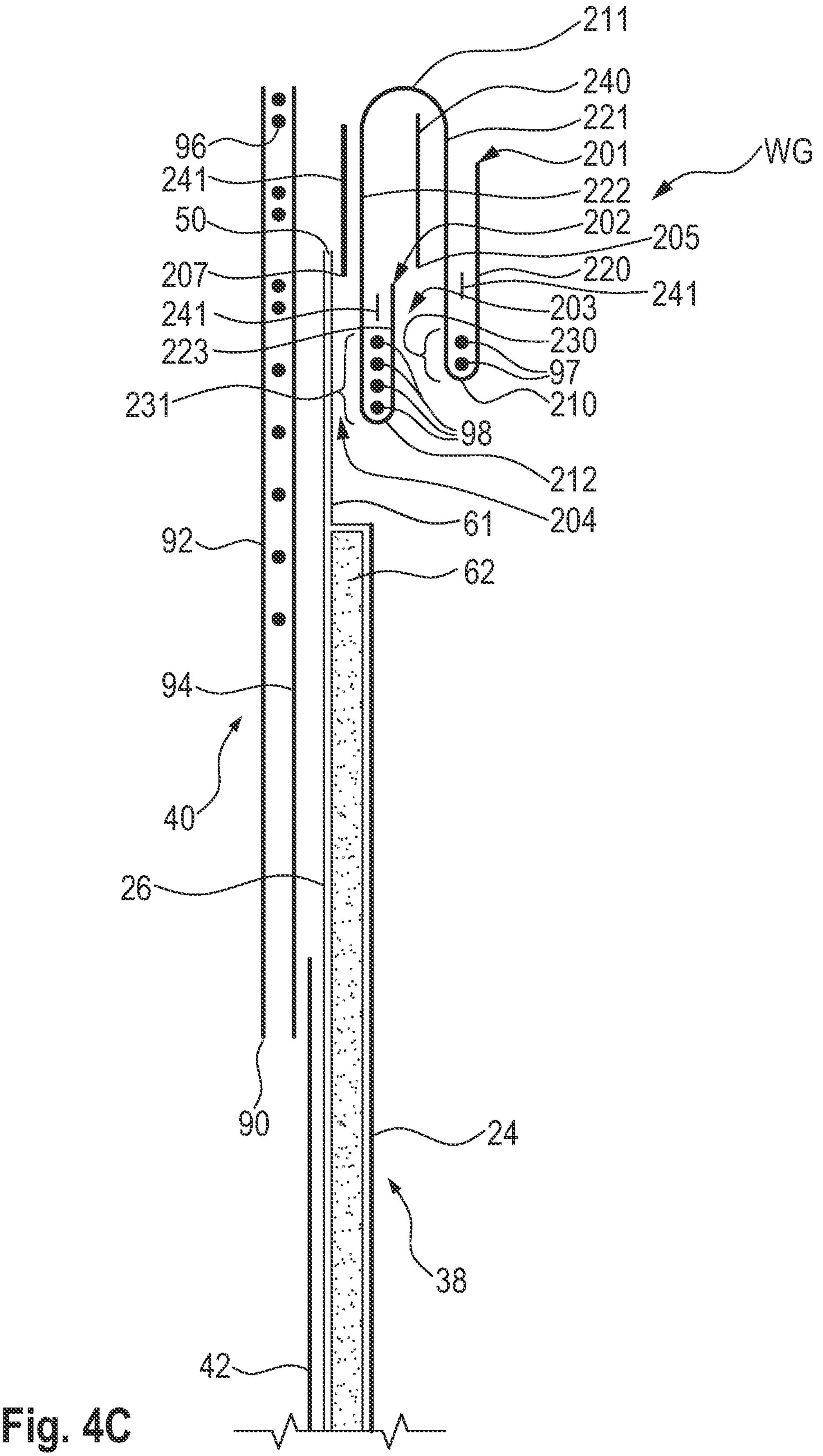
Figure 4D:
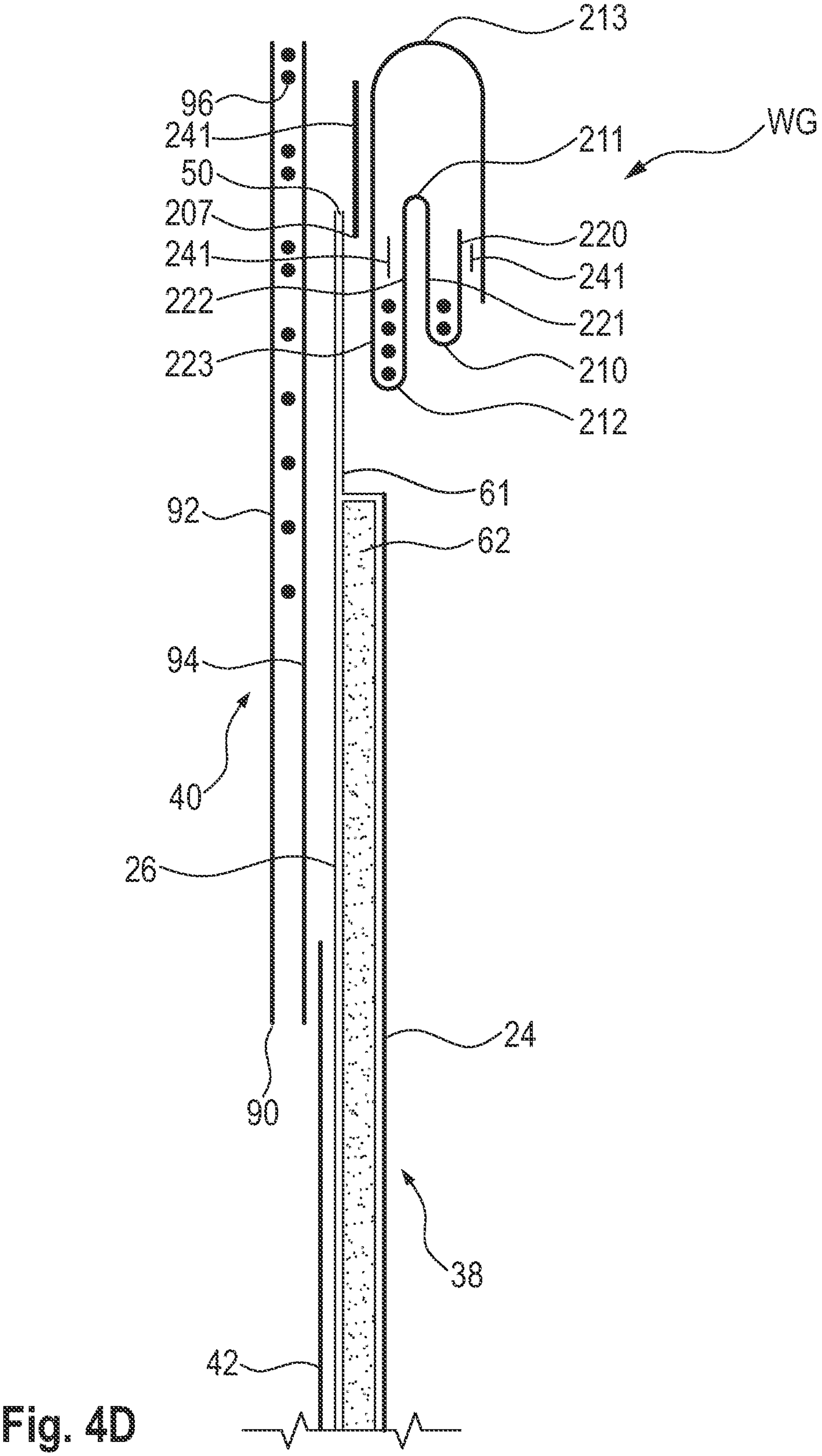
Figure 4E:
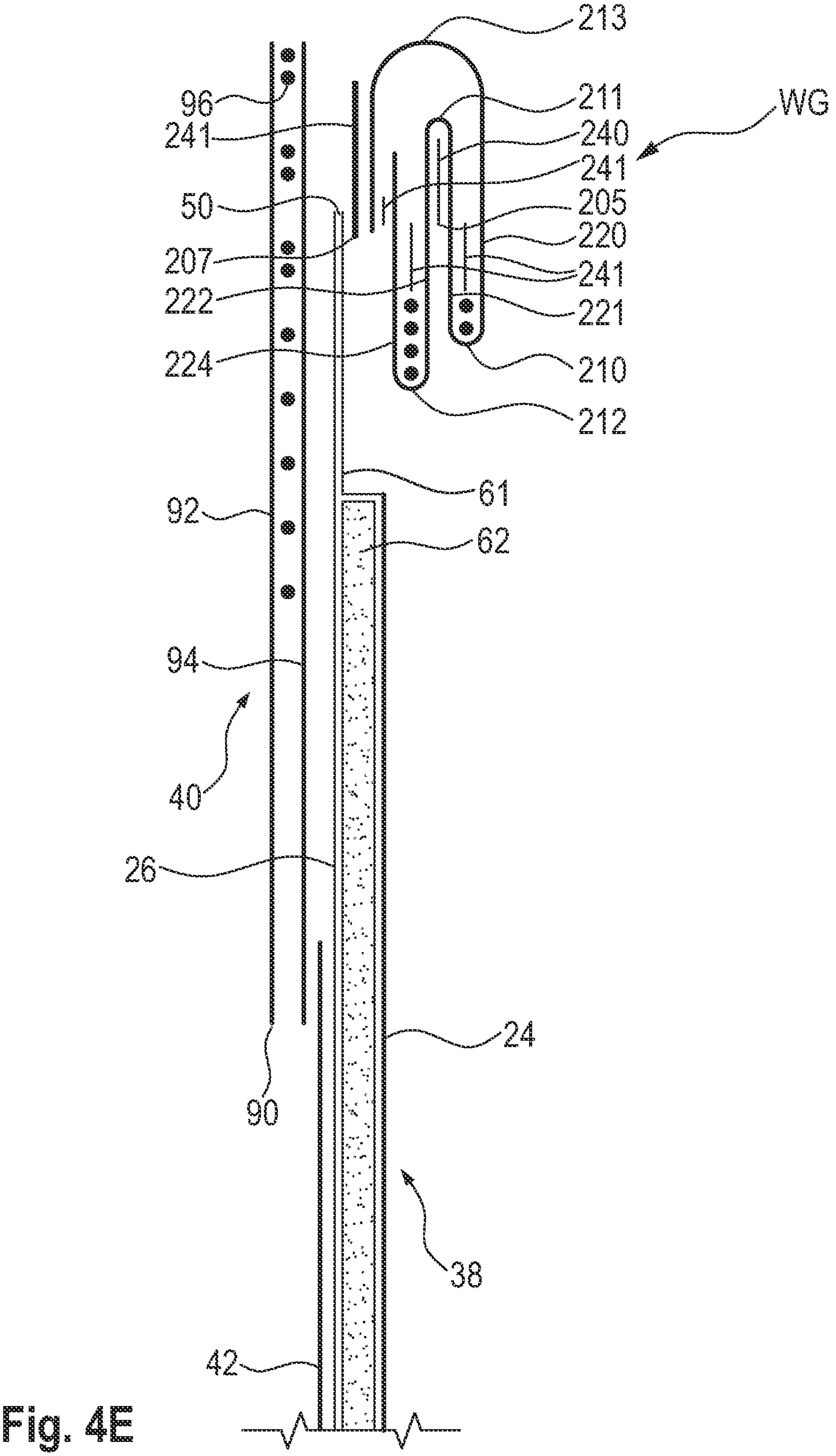
Figure 4F:
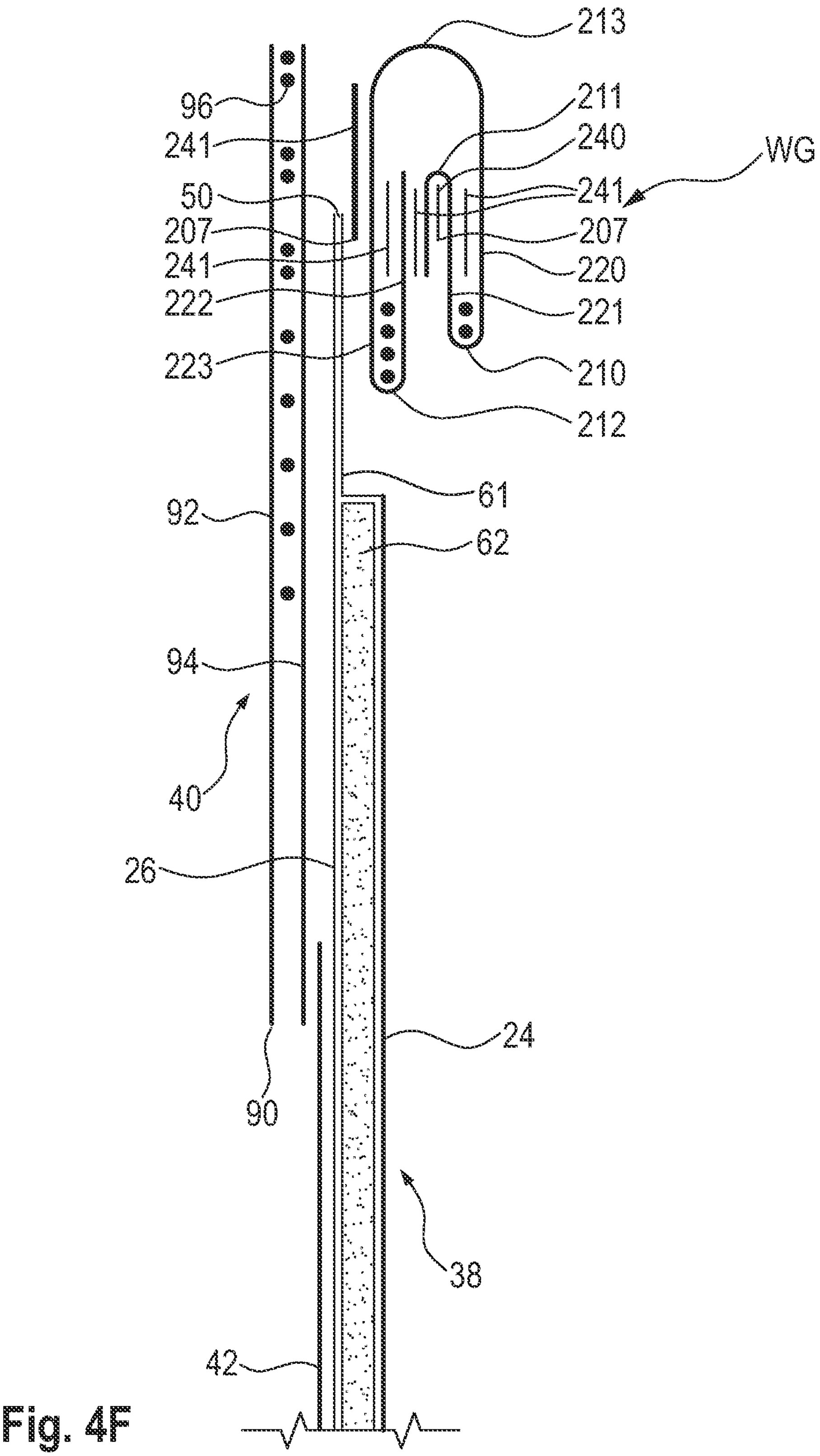
Figure 4G:
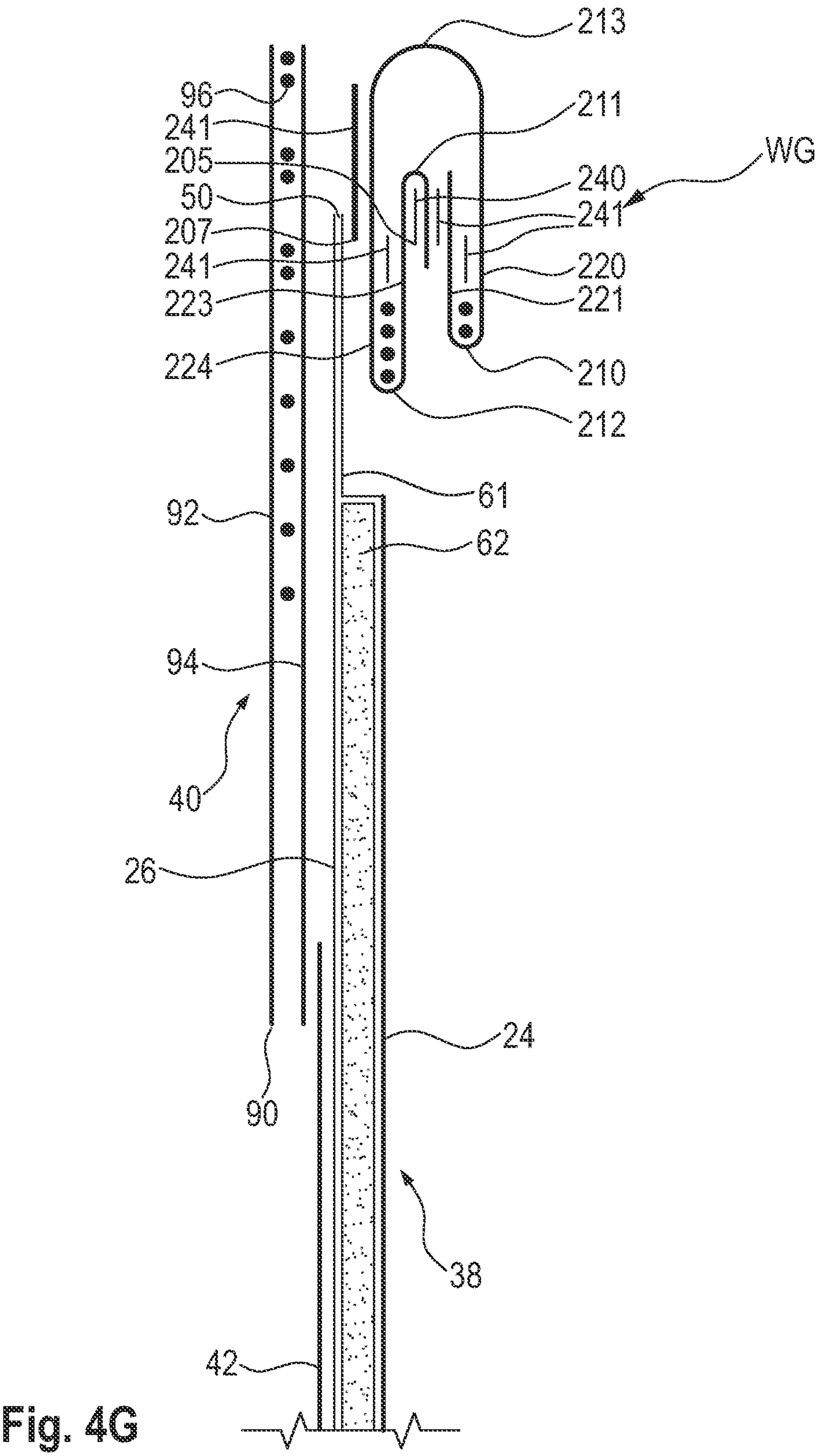

A part of the first portion 220 and a part of the second portion 221 may form body-facing boundaries of the first pocket 203, as illustrated in FIGS. 2, 4A, and 4G. Alternatively, the body-facing boundaries of the first pocket 203 may only be formed by the second portion 221 of the waist guard sheet 200, as shown in FIGS. 4B, 4C, 4D, 4F and 4E.

Also, a part of the third portion 222 and a part of the fourth portion 223 may form the garment-facing boundaries of the first pocket 203, as exemplified in FIGS. 4A and 4C. Alternatively, the garment-facing boundaries of the first pocket 203 may only be formed by the third portion 222 of the waist guard sheet 200, as shown in FIGS. 2, 4B, 4D. 4G, 4F and 4E. In a still further alternative, the garment-facing boundaries of the first pocket 203 may only be formed by the fourth portion 223 of the waist guard sheet 200.

At least a part of fourth portion 223, at least a part of the third portion 222, or both, may be directly attached to the topsheet 24. Also, another part of the fourth portion 223, another part of the third portion 222, or both, may be directly attached to the leg cuffs 64 of the absorbent article 20.

The waist guard WG may be attached to the absorbent article 20 such that the attachment is longitudinally spaced from the third fold line 212 towards the back waist edge 37. Thereby, the waist guard sheet 200 is comprised by the second pocket 204. The third fold line 212 may define the second open edge 208 of the second pocket 204.

A part of the third portion 222 and a part of the fourth portion 223 may form body-facing boundaries of the second pocket 204, as illustrated in FIG. 4B. Alternatively, the body-facing boundaries of the second pocket 204 may only be formed by the third portion 222 of the waist guard sheet 200, as shown in FIGS. 2 and 4A. Still alternatively, the body-facing boundaries of the second pocket may only be formed by the fourth portion of the sheet, as shown in FIGS. 4B, 4C, 4D, 4E, 4F and 4G.

Also, the topsheet 24 may form the garment-facing boundaries of the second pocket 204, as exemplified in FIGS. 2 and 4A to 4G.

The second pocket 204 may not be in direct contact with the first portion 220 and the second portion 221 of the waist guard sheet 200.

Hence, the first and second pocket may be provided adjacent to each other (one on top of each other in the direction that is perpendicular to the longitudinal and transverse direction of the absorbent article). They may be formed by a single waist guard sheet 200, such as by a single nonwoven web. The third and fourth portion 222, 223 of the waist guard sheet 200 may be provided in between the first and second pocket 203, 204 and delimit the first pocket 203 from the second pocket 204. By having a first and second pocket 203, 204, the total volume inside the waist guard WG for containing feces can be increased. Providing two pockets rather than one large pocket, can help to savely keep the feces inside the pockets. Also, the overall volume of a single pocket has a kind of construction-conditioned upper limit based on the overall dimensions of the absorbent article, as the open edge of the pocket can not be provided arbitrarily close towards the transverse centerline of the absorbent article. If the open edge is provided too close towards the transverse centerline, the waist guard will cover an overly large part of the wearer's gluteal grove, and may consequently not be able to efficiently capture lose feces.

The third fold line 212 may be provided closer to the transverse centerline than the first fold line 210. Thereby, the topsheet 24 does not form a boundary of the first pocket 203, i.e., the first pocket 203 is not in direct contact with the topsheet 24. This configuration helps to safely maintain feces captured inside the first pocket 203. Also, it has been found that the first pocket 203 may not open properly during use if the first fold line 210 is provided closer to the transverse centerline than the third fold line 212. In fact, also the proper opening of the second pocket 204 may be hampered if the first fold line 210 is provided closer to the transverse centerline than the third fold line 212.

The waist guard WG may comprise a fourth fold line 213. A waist guard WG comprising a fourth fold line 213 is exemplified but not limited to the embodiments shown in FIGS. 4D, 4E, 4F and 4G.

The optional fourth fold line 213 is provided towards the back waist edge 37. The fourth fold line 213 may coincide with the back waist edge 37 of the absorbent article 20, or may be, at least slightly, longitudinally offset from the back waist edge 37 towards the transverse centerline. If the wait guard WG comprises a fourth fold line 213, the second fold line 211 is provided closer to the transverse centerline than the fourth fold line 213 (while the first and third fold line 210, 212, are always provided closer to the transverse centerline than the second fold line 211).

If the waist guard WG comprises a fourth fold line 213, the fourth portion 223 extends between the third fold line 212 and the fourth fold line 213.

If the waist guard WG comprises a fourth fold line 213, one of the first, second, third and fourth portion 220, 221, 222, 223, may not formed of a continuous section of the waist guard sheet 200. Instead, one of the first, second, third and fourth portion 220, 221, 222, 223 may comprise the first and the second end edge 201, 202 of the waist guard sheet 200.

The first and second end edges 201, 202 may overlap (exemplified but not limited to the embodiments shown in FIGS. 4D, 4E, 4F and 4G). The overlapping areas of the waist guard sheet 200 adjacent to the first and second end edges 201, 202 may be attached to each other. Attachment may be done by any means known in the art, such as by adhesive, thermal bonding, pressure bonding, ultrasonic bonding, or combinations thereof.

The waist guard WG comprises a second elastic portion 231. The second elastic portion 231 being provided along and/or adjacent to the the second open edge 208. The second open edge may be formed by the third fold line 212. The second elastic portion 231 is thus comprised by the first pocket 203 and also by the second pocket 204. The second elastic portion 231 ensures that the second pocket 204 can open properly and thus can efficiently receive lose feces.

A non-elastic portion may be provided at or adjacent to the second fold line 211. The second fold line 211 may form the first closed base line 205 of the first pocket 203.

While elasticity is desirable at or adjacent the fold lines which form the first and/or second open edge 206, 208, of the first and/or second pocket 203, 204 to ensure proper opening of the pocket(s) during use, it is preferred that the area at and towards the first and/or second closed based line 205, 207, of the first and/or second pocket(s) has no elasticity or reduced elasticity. Otherwise, the full capacity (i.e., the complete volume) of the pocket(s) may not be available for capturing feces.

It is desirable that the first and second elastic portion 230, 231 are provided with elastic strands placed between the respective portions of the waist guard sheet 200.

The first elastic portion 230 may comprise one or more elastic strands 97 which are provided between the first and second portion 220, 221 of the waist guard sheet 200, the one or more elastic strands 97 of the first elastic portion 230 extending along the transverse direction of the absorbent article 20. The one or more elastic strands 97 of the first elastic portion 230 may preferably be provided such that the waist guard sheet 200 is gathered when the elastic strands 97 are in their relaxed state (i.e. not stretched by application of a force). "Gathered" means that the waist guard sheet 200 is formed with wrinkels. Such wrinkles, at least partly, disappear when the elastic strands are stretched out. Consequently, the elastic strands 97 of the first elastic portion 230 may be applied to the waist guard sheet 200 (e.g. by adhesively attaching the elastic strands 97 to the waist guard sheet 200) while the elastic strands 97 are in an extended, stretched condition. The elastic strands 97 which are comprised by the first elastic portion 230 are preferably attached to the waist guard sheet 200 prior to forming the first fold line 210.

There may be 2 to 10 elastic strands 97, or from 2 to 8 elastic strands, or 3 to 6 elastic strands, or 3 to 5 elastic strands in the first elastic portion 230.

The distance between the two elastic strands (of the first elastic portion) which are closest to the first open edge 206 may be smaller than the distance between any other neighboring elastic strands in the first elastic portion 230. Alternatively or in addition, the distance between the first open edge 206 and the elastic strand (of the first elastic portion) closest to the first open edge 206 may be the same or smaller than the distance between the two elastic strands (of the first elastic portion) which are closest to the first open edge 206. Also alternatively or in addition, the number of elastic strands (of the first elastic portion) adjacent the first fold line may be higher than the number of elastic strands (of the first elastic portion) away from the first open edge 206, wherein "away from the first open edge" means the 50% of the first pocket which are furthest away from the first open edge 206.

Similarly, the second elastic portion 231 may comprise one or more elastic strands 98 which are provided between the third and fourth portion 222, 223 of the waist guard sheet 200, the one or more elastic strands 98 of the second elastic portion 231 extending along the transverse direction of the absorbent article 20. The one or more elastic strands 98 of the second elastic portion 231 are preferably provided such that the waist guard sheet 200 is gathered when the elastic strands 98 are in their relaxed state (i.e. not stretched by application of a force). Consequently, the elastic strands 98 of the second elastic portion 231 may be applied to the waist guard sheet 200 (e.g. by adhesively attaching the elastic strands to the waist guard sheet) while the elastic strands 98 are in a stretched condition. The elastic strands 98 which are comprised by the second elastic portion 231 are preferably attached to the waist guard sheet 200 prior to forming the second open edge 208.

There may be 2 to 10 elastic strands 98, or from 2 to 8 elastic strands, or 3 to 6 elastic strands, or 3 to 5 elastic strands in the second elastic portion.

The distance between the two elastic strands (of the second elastic portion) which are closest to the second open edge 208 may be smaller than the distance between any other neighboring elastic strands in the second elastic portion. Alternatively or in addition, the distance between the second open edge 208 and the elastic strands (of the second elastic portion) closest to the second open edge 208 may be the same or smaller than the distance between the two elastic strands (of the second elastic portion) which are closest to the second open edge 208. Also alternatively or in addition, the number of elastic strands (of the second elastic portion) adjacent the second open edge 208 may be higher than the number of elastic strands (of the second elastic portion) away from the second open edge 208, wherein "away from the second open edge" means the 50% of the first pocket which are furthest away from the second open edge 208.

The plurality of elastic strands 97 of the first elastic portion 230 may be spaced from the first open edge 206 at a distance of not more than about 12 mm, preferably not more than about 10 mm, more preferably not more than 5 mm.

Likewise, the plurality of elastic strands 98 of the second elastic portion 231 may be spaced from the second open edge 208 at a distance of not more than about 12 mm, preferably not more than about 10 mm, more preferably not more than 5 mm.

The longitudinal dimension of the first pocket 203, defined as the shortest distance between the first closed base line 205 to the first open edge 206, may be from about 10 mm to about 60 mm, preferably from 12 mm to 40 mm, still more preferably from 20 mm to 30 mm.

The longitudinal dimension of the second pocket 204, defined as the shortest distance between the second closed base line 207 to the second open edge 208, may be from about 10 mm to about 60 mm, preferably from 12 mm to 40 mm, still more preferably from 20 mm to 30 mm.

The longitudinal dimension of the second pocket 204 may be from 5 mm to 40 mm, or from 8 mm to 25 mm, or from 10 mm to 20 mm longer than the longitudinal dimension of the first pocket 203.

The transverse dimension of the first pocket 203 is defined as the longest distance of the first pocket 203 extending parallel to the transverse centerline of the absorbent article 20 from the left side edge of the first pocket 203 to the right side edge of the first pocket 203. The left and right side edges of the first pocket 203 extend between the first closed base line 205 and the first open edge 206. The transverse dimension of the first pocket 203 (=the width of the first pocket 203) may be from 40% to 96%, or from 50% to 95%, or from 60% to 95% of the transverse dimension of the transversely extending edge of the backsheet 26 (=the width of the backsheet 26), which is provided in the back waist region 36. The transversely extending edge of the backsheet 26 in the back waist region 36 may extend parallel to the transverse centerline of the absorbent article 20.

The transverse dimension of the first pocket 203 may be from 40 mm to 200 mm, or from 50 mm to 180 mm, or from 60 mm to 140 mm. The first pocket 203 may have a smallest distance extending parallel to the transverse centerline of the absorbent article 20 from the left side edge of the first pocket 203 to the right side edge of the first pocket 203, which may be the same as the longest distance of the first pocket 203 (such that there is no difference between longest and shortest distance), or the shortest distance of the first pocket 203 may be at least 70%, or at least 80%, or at least 90% of the longest distance of the first pocket 203.

The transverse dimension of the second pocket 204 is defined as the longest distance of the second pocket 204 extending parallel to the transverse centerline of the absorbent article 20 from the left side edge of the second pocket 204 to the right side edge of the second pocket 204. The left and right side edges of the second pocket 204 extend between the second closed base line 207 and the second open edge 208. The transverse dimension of the second pocket 204 (=the width of the second pocket 204) may be from 40% to 96%, or from 50% to 95%, or from 60% to 95% of the transverse dimension of the transversely extending edge of the backsheet 26 (=the width of the backsheet 26), which is provided in the back waist region 37. The transversely extending edge of the backsheet 26 in the back waist region 37 may extend parallel to the transverse centerline of the absorbent article 20.

The transverse dimension of the second pocket 204 may be from 40 mm to 200 mm, or from 50 mm to 180 m, or from 60 mm to 140 mm. The second pocket 204 may have a smallest distance extending parallel to the transverse centerline of the absorbent article 20 from the left side edge of the second pocket 204 to the right side edge of the second pocket 204, which may be the same as the longest distance of the second pocket 204 (such that there is no difference between longest and shortest distance), or the shortest distance of the second pocket 204 may be at least 70%, or at least 80%, or at least 90% of the longest distance of the second pocket 204.

The first pocket and/or the second pocket 203, 204 may have a rectangular shape.

The front and back elastic belts 84, 86 may each be divided into multiple zones spanning in the transverse direction and defined by its location from the distal edge 88 to the proximal edge 90 relative to the percentage of the seam length LS wherein the distal edge 88 is considered 0% and the proximal edge 90 is considered 100%. The multiple zones may be configured to provide different tensile stress, or different functions to the front and back elastic belts 84, 86, respectively. In the absorbent article of the present invention, a waist guard WG is disposed. The waist guard WG extends towards the crotch region 30. The waist guard WG may be partially bonded to the remainder of the back elastic belt 84, 86. The waist guard WG may be disposed within a location of 0-60% of LS on the back elastic belts 84, 86. FIG. 1 depicts such waist guard WG on the back elastic belt. The waist guard WG may be shorter, such that it spans less than the entire 0-60% of LS. The waist guard WG may be positioned at a dimension of from from about 0% to about 55% of LS, or from about 0% to about 50% of LS, or from about 100% to about 55% of LS, or from about 0% to about 50% of LS, i.e. the entire waist guard WG may be provided within these preferred ranges. Without being bound by theory, by providing the waist guard WG in such dimension on the back elastic belt 86, the buttock cleavage of a wearer is effectively covered by the waist guard WG so that low viscosity exudate, such as runny fecal matter or blood, may be effectively drawn into the first and the second pocket 203, 204.

As exemplarily shown in FIGS. 1 and 2 (but not limited to the embodiment illustrated in these Figures, but applicable to all absorbent articles of the present invention), the waist guard WG may be made by an extension 93 of the outer sheet 92 extending (prior to being folded) beyond the longitudinal dimension of the inner sheet 94. The extension 93 of the outer sheet 92 is folded inwardly at the outer sheet fold 931 to provide the waist guard WG. If the waist guard WG is made by an extension 93 of the outer sheet 92, the extension 93 of the outer sheet 92 forms the waist guard sheet 200. If the waist guard WG is made by an extension 93 of the outer sheet 92, the waist guard may not comprise a fourth fold line 213.

Referring to FIG. 2, a certain longitudinal dimension from the waist guard sheet 200 (here the waist guard sheet being the folded over extension 93 of the outer sheet) 92 may be bonded to the body-facing surface of the remainder of the back elastic belt 86, such bonding shown as SWFA. However, some dimension may be left unbonded, thereby forming the second pocket 204.

Preferably the bonding is made by adhesive. The adhesive may be hydropobic, which can help to prevent low viscosity exudate from penetrating out of the first and second pocket by penetrationg through the waist guard sheet. The adhesive, such as the hydrophobic adhesive, may be a hot melt adhesive. To determine whether a hot melt adhesive is hydrophobic, a portion of the hot melt adhesive is molten and spread on an even, horizontal surface, such as a table, to form a film. Then a drop of water is applied on the fim and the contact angle is determined, as is well known in the art. The adhesive is hydrophobic, if the contact angle of more than 90°.

The unbonded region thus provided, is defined and delimited by the second closed base line 207 and the left and right transverse edges (delimiting the second pocket 204). The bondings provided to define the area of the second pocket 204 are so configured to provide the second pocket 204 superposing the backsheet 26, preferably completely superposing the backsheet 26 in both in the longitudinal dimension parallel to the longitudinal centerline of the absorbent article as well as in the transverse direction parallel to the transverse centerline of the absorbent article.

The bonded portion (shown as SWFA) the second pocket 204 may superpose the backsheet 26 by at least 5 mm, or by at least 10 mm along each of the left and right side edges of the second pocket 204, wherein the respective part of the edge of the bonded portion may delimit and thus define the left and right side edges of the second pocket 204. Moreover, the bonded portion delimiting the second pocket 204 may superpose the backsheet 26 by at least 5 mm, or by at least 10 mm along the second closed base line 207 of the second pocket 204, wherein the respective part of the edge of the bonded portion may delimit and thus define the second closed base line 207 of the second pocket 204.

For forming the first pocket 203, a certain longitudinal dimension of the second portion 221 of the waist guard sheet 200 may be bonded to the third and/or fourth portion 222, 223 of the waist guard sheet 200 at or adjacent to the second fold line 211, such bonding shown as 240 in FIG. 4B, however, leaving some longitudinal dimension unbonded, thereby defining and forming the first pocket 203. The transversely extending edge of such bonded portion delimiting the first pocket 203 is the first closed base line 205. Alternatively (and preferably) the second fold line 211 may form the first closed base line.

The first pocket 203 is defined as having a longitudinal dimension spanning from the first closed base line 205 to the first open edge 206. The left and right transverse edges of the first and/or second portion 220, 221 of the waist guard sheet 200 may be bonded to the third and/or fourth portion 212, 213.

Preferably the bonding is made by adhesive. The adhesive may be hydropobic, which can help to prevent low viscosity exudate from penetrating out of the first and second pocket by penetrationg through the waist guard sheet. The adhesive, such as the hydrophobic adhesive, may be a hot melt adhesive.

The unbonded region thus provided, is defined and delimited by the first closed base line 205 and the left and right transverse edges (delimiting the first pocket 203), is the first pocket 203. The bondinded regions provided to define the area of the first pocket 203 are so configured to provide the first pocket 203 superposing the backsheet 26, preferably completely superposing the backsheet 26 in both in the longitudinal dimension parallel to the longitudinal centerline of the absorbent article as well as in the transverse direction parallel to the transverse centerline of the absorbent article.

The bonded portion delimiting the first pocket 203 may superpose the backsheet 26 by at least 5 mm, or by at least 10 mm along each of the left and right side edges of the first pocket 203, wherein the respective part of the edge of the bonded portion may delimit and thus define the left and right side edges of the first pocket 203. Moreover, the bonded portion delimiting the first pocket 203 may superpose the backsheet 26 by at least 5 mm, or by at least 10 mm along the first closed base line 205 of the first pocket 203, wherein the respective part of the edge of the bonded portion may delimit and thus define the first closed base line 205 of the first pocket 203 (however, as set out above, the first close base line 205 may alternatively be formed by the second fold line 211).

Without being bound by theory, by providing the first and the second pocket substantially superposing the backsheet, prevents low viscosity exudates and/or low surface tension exudates having entered the pocket(s) from flowing or penetrating out of the pocket(s) through the layers underneath the pocket(s), i.e. in the direction perpendicular to the longitudinal and transverse centerline and towards the garment-facing surface of the absorbent article.

The first and the second pocket 203, 204 may each have a rectangular shape (as exemplarily shown in FIGS. 2B and 2C but not limited to the embodiments illustrated in these figures), however, the first and/or second pocket may take other shapes by changing the bonding area such that the first and/or second closed base line 205, 207, and/or the left and right transverse edges defining the first and/or second pocket 203, 204, are shaped. For example, the first and/or second closed base line 205, 207 may be concave or convex toward the pocket to match the wearer's anatomy. The first and/or second closed base line 205, 207 may also be straight and parallel to the distal edge 88 of the back elastic belt 86 (i.e. parallel to the back waist edge 37 of the absorbent article). This may e.g. be the case if the first closed base line 205 is formed by a third fold line. The left and right transverse edges may be such that the width of the first and/or second pocket 203, 204 increases or decreases along the longitudinal dimension starting from the first and/or second closed base line 205, 207 to the first and/or second open edge 206, 208 of the first and/or second pocket 203, 204.

The longitudinal dimension of the first pocket 203 is defined as the shortest distance between the first closed base line 205 to the first open edge 206 and extending parallel to the longitudinal centerline of the absorbent article.

The longitudinal dimension of the second pocket 204 is defined as the shortest distance between the second closed base line 207 to the second open edge 208 and extending parallel to the longitudinal centerline of the absorbent article.

The waist guard WG is preferably provided such that the first and the second pocket 203, 204 are provided at a dimension of from about 5% to about 60%, preferably to about 55% and more preferably to about 50% of LS. By providing the first and second pocket 203, 204 at a dimension of from about 5% to about 60%, preferably to about 55% and more preferably to about 50% of LS, the pocket(s) is (are) provided such that the likelihood of the first and second open edge 206, 208 of the first and second pocket 203, 204 overlaying the gluteal grove of the wearer is reduced. The article of the present invention is (also) suitable for baby/toddler pants which are already more active compared to new born babies. However, increased activity generally leads to a higher likelihood that the article sags, so that the waist edge (=distal edge of the front and back belt) shifts downwardly during use. Thereby, also the waist guard, including the first and second open edges, tends to shift downwardly during use. To address and counterbalance such movement, the first and second open edges may be provided sufficiently high (in the longitudinal dimension, i.e. towards the distal edge of the back belt) to reduce or avoid the risk of overlap of the first and second open edge with the gluteal grove. If the first and second open edge overlaps with the gluteal grove, the pocket may not able be to properly receive fecal material.

As exemplified in FIG. 2 (but not limited to the embodiment shown in this Figure, but applicable to all absorbent articles of the present invention), the area of the back elastic belt 86 superposing the first and second elastic portion 230, 231 is defined a correlated portion 232. The correlated portion 232 may be elasticized or may not be elasiticized. The tensile stress of the first and second elastic portion 230, 231 may be different than that of the correlated portion 232. The difference in tensile stress of the waist guard elastic portion WGEP to the correlated portion CP may be at least about 25%, or at least about 50%, or at least about 70%. Without being bound by theory, such tensile stress difference enables the first and second elastic portions to be in close contact with the wearer, while pulling away the first and second open edges from the correlated portion, thus opening the first and the second pocket. Thus, the first and the second pocket are configured to have good containment capacity.

The absorbent core 62 may partially superpose the area of the first and the second pocket 203, 204 to provide at least some absorbent capacity in this region. At least about 3%, or at least about 10%, or at least 20%, or at least 30%, or at least 40% of the area of the first pocket 203 and at least about 3%, or at least about 10%, or at least 20%, or at least 30%, or at least 40% of the area of the second pocket 204 may superpose the absorbent core 62. Even so, the combined thickness of the waist guard WG, the correlated portion 232 of the back elastic belt 86, and the portion of the absorbent main body 38 sandwiched therebetween may be kept to no more than about 5 mm, preferably no more than about 4 mm. This is so that the thickness of the article does not interfere with the opening of the first and the second pocket.

Barrier Leg Cuffs and Leg Elastics

The absorbent main body 38 of the absorbent article may comprise one or more pairs of barrier leg cuffs 64 and one or more pairs of leg elastics. The barrier leg cuffs 64 may be positioned laterally inboard of leg elastics. Each barrier leg cuff 64 may be formed by a piece of material which is bonded to the absorbent main body 38 so it extends upwards from a body-facing surface of the absorbent main body 38 when the absorbent article is worn, and provide improved containment of body exudates approximately at the junction of the torso and legs of the wearer. The barrier leg cuffs 64 are delimited by a proximal edge joined directly or indirectly to the topsheet 24 and/or the backsheet 26 and a free terminal edge, which is intended to contact and form a seal with the wearer's skin. The barrier leg cuffs 64 may extend at least partially between the front and back transversely extending end edges 50 of the absorbent main body 38 along and adjacent to each of the two side edges 48 of the absorbent main body 38 and may be at least present in the crotch region 30, and may extend into the front and back waist region 34, 36. The barrier leg cuffs 64 may each comprise one or more elastics (e.g., elastic strands or strips) near or at the free terminal edge. These elastics cause the barrier leg cuffs to help form a seal around the legs and torso of a wearer. The leg elastics extend at least partially between the two transversely extending end edges 50 of the absorbent main body 38. The leg elastics essentially cause portions of the absorbent article proximate to the absorbent main body's two (i.e. left and right) side edges 48 to help form a seal around the legs of the wearer. The leg elastics may extend at least within the crotch region 30.

At least a part of waist guard sheet 200 may be directly attached to the barrier leg cuffs 64. For example, at least a part of the fourth portion 223, at least a part of the third portion 222, or both, may be directly attached to the topsheet 24; and at least a part of fourth portion 223, at least a part of the third portion 222, or both, may be directly attached to the barrier leg cuffs 64.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal centerline and a longitudinal direction along and in parallel to the longitudinal centerline; a transverse centerline and a transverse direction along and in parallel to the transverse centerline, a front waist region with a front waist edge, a back waist region with a back waist edge and a crotch region extending longitudinally between the front and back waist region, the absorbent article comprising an absorbent main body, the absorbent main body comprising a topsheet, a backsheet, and an absorbent core sandwiched there between;

wherein a waist guard is disposed in and attached to the back waist region, the waist guard comprising one or more waist guard sheets, and the waist guard comprising at least a first and a second pocket, the first pocket being formed by the one or more waist guard sheets, and the second pocket being at least partially provided between the topsheet and the first pocket;

the first pocket having a first closed base line adjacent to the back waist edge and extending along the longitudinal direction from the first closed base line towards a first open edge, and the second pocket having a second closed base line at or adjacent to the back waist edge and extending along the longitudinal direction from the second closed base line towards a second open edge, wherein the complete area of each of the first pocket and of the second pocket superposes the backsheet;

wherein the first pocket comprises at least a first elastic portion provided at or adjacent to the first open edge and the second pocket comprises at least a second elastic portion provided at or adjacent to the second open edge, wherein the second open edge is provided closer to the transverse centerline than the first open edge.

2. The absorbent article of claim 1, wherein the waist guard is formed by one or more waist guard sheets with the first and second elastic portions each comprising one or more than one elastic strands which are provided between layers of the one or more waist guard sheets, the layers of the one or more waist guard sheets being formed by folding the one or more waist guard sheets, the elastic strands extending along the transverse direction of the absorbent article.

3. The absorbent article of claim 2, wherein, of the plurality of elastic strands of the first elastic portion, the elastic strand closest to the first open edge is spaced from the first open edge at a distance of not more than about 12 mm; and wherein, of the plurality of elastic strands of the second elastic portion, the elastic strand closest to the second open edge is spaced from the second open edge at a distance of not more than 12 mm.

4. The absorbent article of claim 1, wherein the waist guard is formed by a single waist guard sheet.

5. The absorbent article of claim 4, wherein the single waist guard sheet has at least three fold lines, the fold lines extending parallel to the transverse direction of the absorbent article, with a first and a third fold line both provided towards the crotch region, a second fold line provided towards the back waist edge, the first fold line defining the first open edge of the first pocket and third fold line defining the second open edge of the second pocket.

6. The absorbent article of claim 5, wherein a non-elastic portion is provided at or adjacent to the second fold line.

7. The absorbent article of claim 6, wherein the second fold forms the first closed base line of the first pocket.

8. The absorbent article of claim 7, wherein the sheet comprises at least a first, second, third and fourth portion, the first portion extending from the first fold line towards the back waist edge, the second portion extending between and being confined by the first fold line and the second fold line, the third portion extending between and being confined by the second fold line and the third fold line; and the fourth portion extending from the third fold line towards the back waist edge, wherein the fourth portion is between the topsheet and the first portion.

9. The absorbent article of claim 8, wherein the absorbent article further comprises barrier leg cuffs and wherein at least a part of fourth portion and at least a part of the third portion are directly attached to the topsheet; and wherein at least a part of fourth portion and at least a part of the third portion are directly attached to the barrier leg cuffs.

10. The absorbent article of claim 9, wherein the first pocket is formed between the second portion; the third portion, and the fourth portion, such that the first pocket is not in direct contact with the topsheet.

11. The absorbent article of claim 10, wherein the waist guard is attached to the topsheet such that a second pocket is formed, the second pocket being formed between the topsheet, the third portion, and the fourth portion, such that the second pocket is not in direct contact with the first portion and the second portion.

12. The absorbent article of claim 1, wherein the longitudinal dimension of the first pocket defined as the longest distance between the first closed base line and the first open edge is from about 10 mm to about 50 mm, and wherein the longitudinal dimension of the second pocket defined as the longest distance between the second closed base line and the second open edge is from 8 mm to 30 mm longer than the longitudinal dimension of the first pocket.

13. The absorbent article of claim 1, wherein the transverse dimension of each of the first and second pocket is from 40 mm to 120 mm.

14. The absorbent article of claim 1, wherein the absorbent article is an absorbent pant, wherein the absorbent pant comprises a front elastic belt provided as the front waist region, a back elastic belt provided as the back waist region, the front and back elastic belt being joined to each other along side seams, forming a waist opening, and a pair of leg openings, with the crotch region extending longitudinally between the front elastic belt and the back elastic belt; the absorbent main body extending the entire longitudinal dimension of the crotch region and further extending partly into each of the front elastic belt and the back elastic belt.

15. The absorbent article of claim 14, wherein the waist guard is partially bonded to the back elastic belt, such that the bonded portion of the waist guard superposes the backsheet by at least 3 mm along each of left and right side edges of the second pocket, thereby defining the left and right side edges of the second pocket.

16. The absorbent article of claim 15, wherein the front elastic belt and the back elastic belt each comprise an inner sheet and an outer sheet, wherein the waist guard sheet is an extension of the outer sheet of the back elastic belt, wherein the extension is folded over inwardly to a body-facing surface of the absorbent article, such that the fold line of the extension forms the back waist edge of the absorbent article.

* * * * *